(12) United States Patent
Schwab

(10) Patent No.: US 10,561,250 B2
(45) Date of Patent: Feb. 18, 2020

(54) CONVERTIBLE PERSONAL MULTIMEDIA POD

(71) Applicant: Jason Schwab, Chicago, IL (US)

(72) Inventor: Jason Schwab, Chicago, IL (US)

( * ) Notice: Subject to any disclaimer, the term of this patent is extended or adjusted under 35 U.S.C. 154(b) by 293 days.

(21) Appl. No.: 15/586,682

(22) Filed: May 4, 2017

(65) Prior Publication Data

US 2017/0318975 A1 Nov. 9, 2017

Related U.S. Application Data

(60) Provisional application No. 62/333,728, filed on May 9, 2016.

(51) Int. Cl.
| | |
|---|---|
| *A61M 21/02* | (2006.01) |
| *A47C 7/72* | (2006.01) |
| *A47C 3/18* | (2006.01) |
| *A47C 7/00* | (2006.01) |
| *A47C 31/00* | (2006.01) |
| *A47C 7/74* | (2006.01) |
| *A61M 21/00* | (2006.01) |
| *B60B 33/00* | (2006.01) |

(52) U.S. Cl.
CPC .................. *A47C 7/72* (2013.01); *A47C 3/18* (2013.01); *A47C 7/006* (2013.01); *A47C 7/725* (2013.01); *A47C 7/744* (2013.01); *A47C 7/748* (2013.01); *A47C 31/005* (2013.01); *A61M 21/0094* (2013.01); *A61M 21/02* (2013.01); *A61M 2021/005* (2013.01); *A61M 2021/0016* (2013.01); *A61M 2021/0027* (2013.01); *A61M 2021/0066* (2013.01); *A61M 2202/0208* (2013.01); *A61M 2205/362* (2013.01); *A61M 2205/3606* (2013.01); *A61M 2205/3653* (2013.01); *A61M 2205/42* (2013.01); *A61M 2205/8293* (2013.01); *B60B 33/0094* (2013.01); *B60B 2200/22* (2013.01)

(58) Field of Classification Search
CPC .. A61M 2202/0007; A61M 2021/0016; A61M 2021/0027; A61M 2021/005; A61M 2021/0066; A61M 21/0094; A61M 21/02; A61M 2205/3606; A61M 2205/42; A61M 2205/8293; A47C 31/005
See application file for complete search history.

(56) References Cited

U.S. PATENT DOCUMENTS

| | | | | |
|---|---|---|---|---|
| 3,826,250 | A * | 7/1974 | Adams | A61M 21/0094 472/136 |
| 5,891,186 | A * | 4/1999 | Daffer | A61H 23/02 600/21 |
| 6,702,767 | B1 * | 3/2004 | Douglas | A61M 21/0094 600/21 |
| 9,084,047 | B2 * | 7/2015 | O'Polka | H04R 1/026 |
| 2011/0051962 | A1 | 3/2011 | Cochran | |
| 2013/0261378 | A1 * | 10/2013 | Habiche | A61H 1/003 600/28 |

FOREIGN PATENT DOCUMENTS

| | | |
|---|---|---|
| CA | 2249065 A1 | 3/2000 |
| CN | 204465767 | 7/2015 |

* cited by examiner

*Primary Examiner* — Christine H Matthews
(74) *Attorney, Agent, or Firm* — Perkins Coie LLP

(57) ABSTRACT

The present disclosure provides personal multimedia pods that convert from an enclosable premium theater system with seating for one or more users to an unenclosed chair and/or to an output audio/video device capable of connecting (e.g., wirelessly connecting) to other audio/visual equipment.

20 Claims, 20 Drawing Sheets

CONVERTIBLE PERSONAL MULTIMEDIA POD

PRIORITY CLAIM

This application claims priority to U.S. Patent Application 62/333,728, filed on May 9, 2016, the entire contents of which are incorporated herein by reference and relied upon.

TECHNICAL FIELD

The present disclosure relates to a personal multimedia pod that converts from an enclosable premium theater system with seating for one or more users to an unenclosed chair and/or to an output audio/video device capable of connecting (e.g., wirelessly connecting) to other audio/visual equipment.

BACKGROUND

Traditional home theater systems are often impractical or disruptive due to the proximity of neighbors, cohabitants, or children. While headphones present one alternative in some situations, most headphones lack the premium sound quality and bass response available through a traditional home theater system. There is a need for a personal multimedia device that provides premium sound quality with the option to enjoy content privately. This need is especially notable as global population numbers swell and urban centers grow; devices consistent with the present disclosure could meet growing demand for personal space in an increasingly connected/urbanized world.

SUMMARY

The present disclosure provides a convertible entertainment pod comprising a shell comprising an inner surface, an outer surface, and a closeable door; a base rotatably affixed to the outside surface of the shell; and a seating portion affixed to or integrated into the inner surface of the shell, wherein the convertible entertainment pod adopts a first, enclosed configuration when the closeable door is in a closed position.

These and other embodiments are described in greater detail below in view of the several drawings.

DETAILED DESCRIPTION

Figure 1:
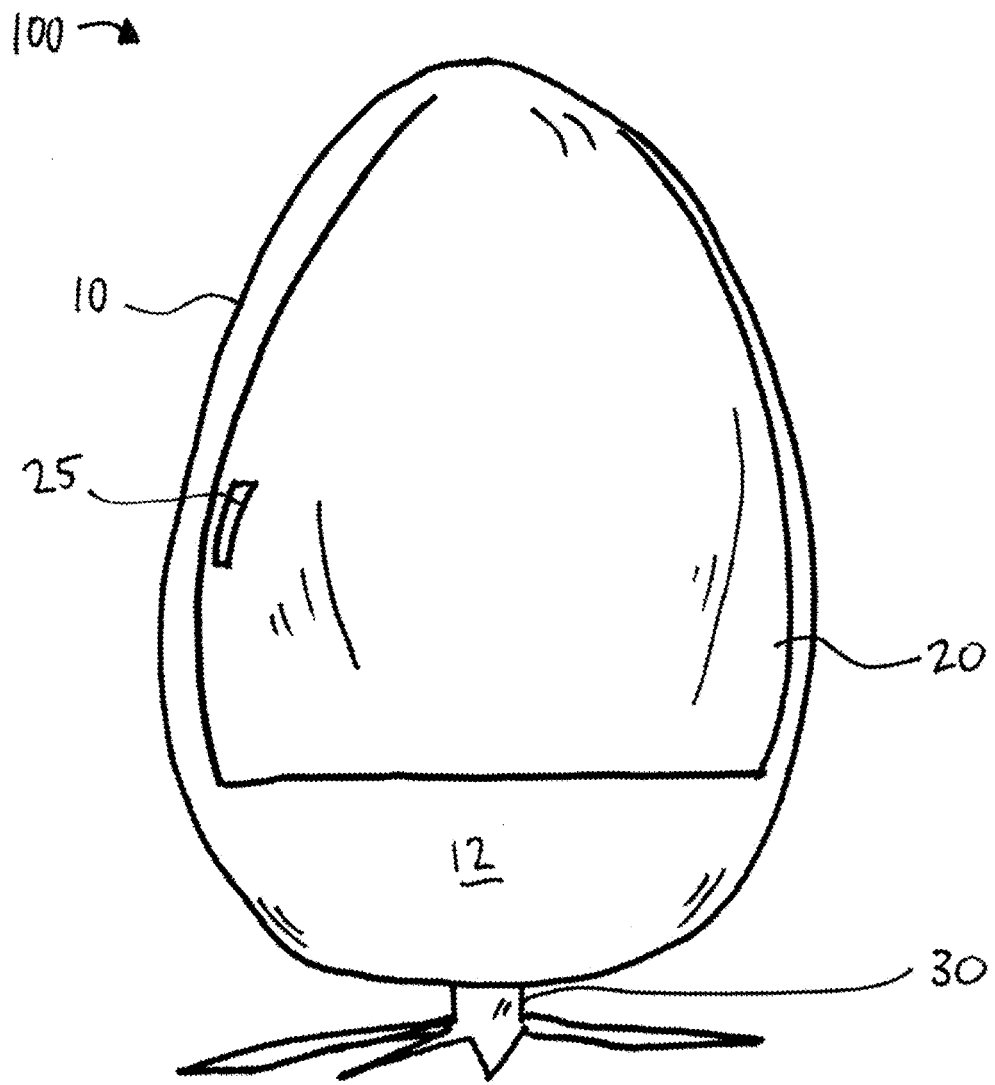
FIG. 1 shows a perspective view of a convertible entertainment pod in an enclosed configuration consistent with one embodiment of the present disclosure.
Figure 2:
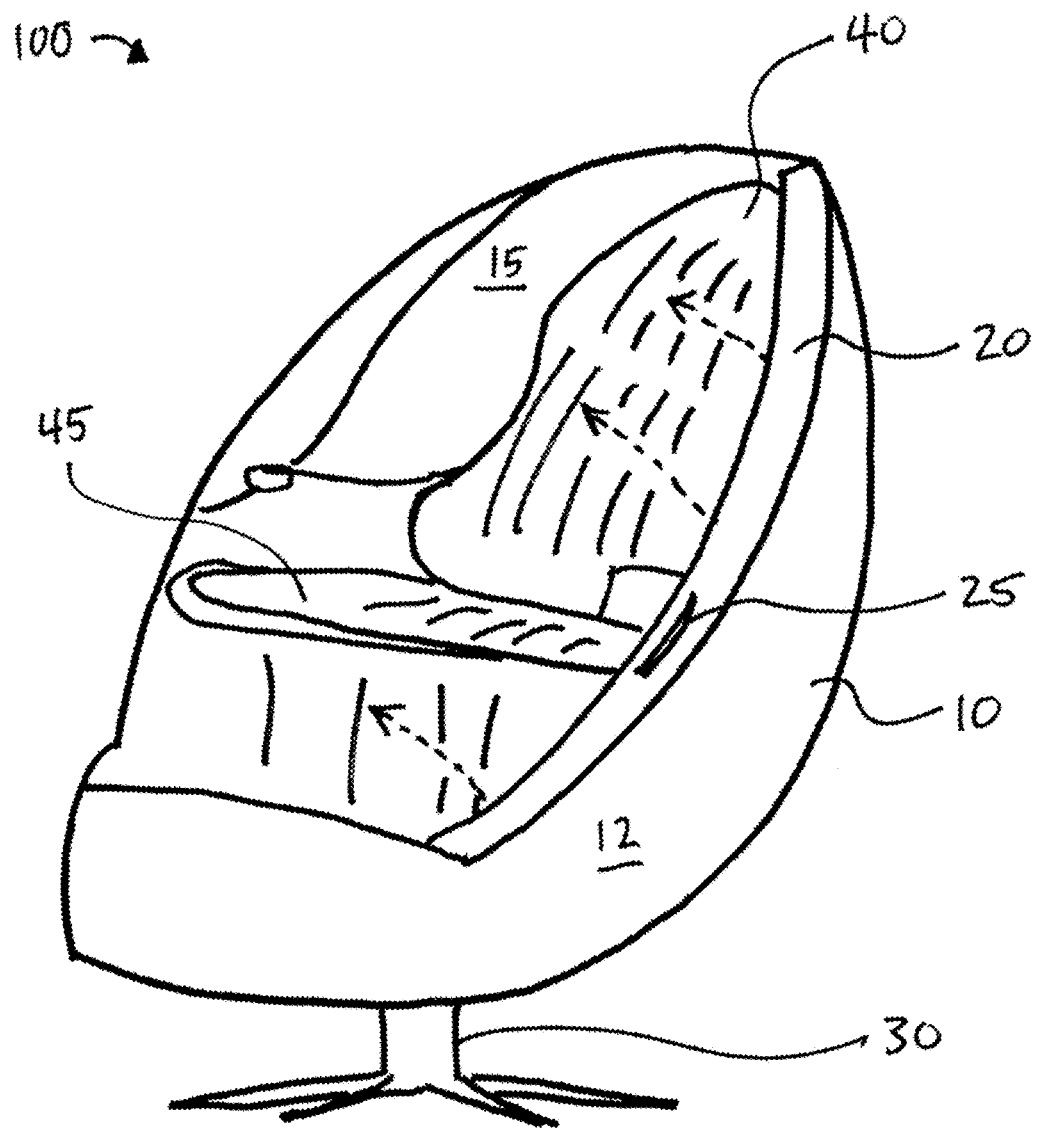
FIG. 2 shows a perspective view of a convertible entertainment pod in an unenclosed or open configuration consistent with one embodiment of the present disclosure.
Figure 3:
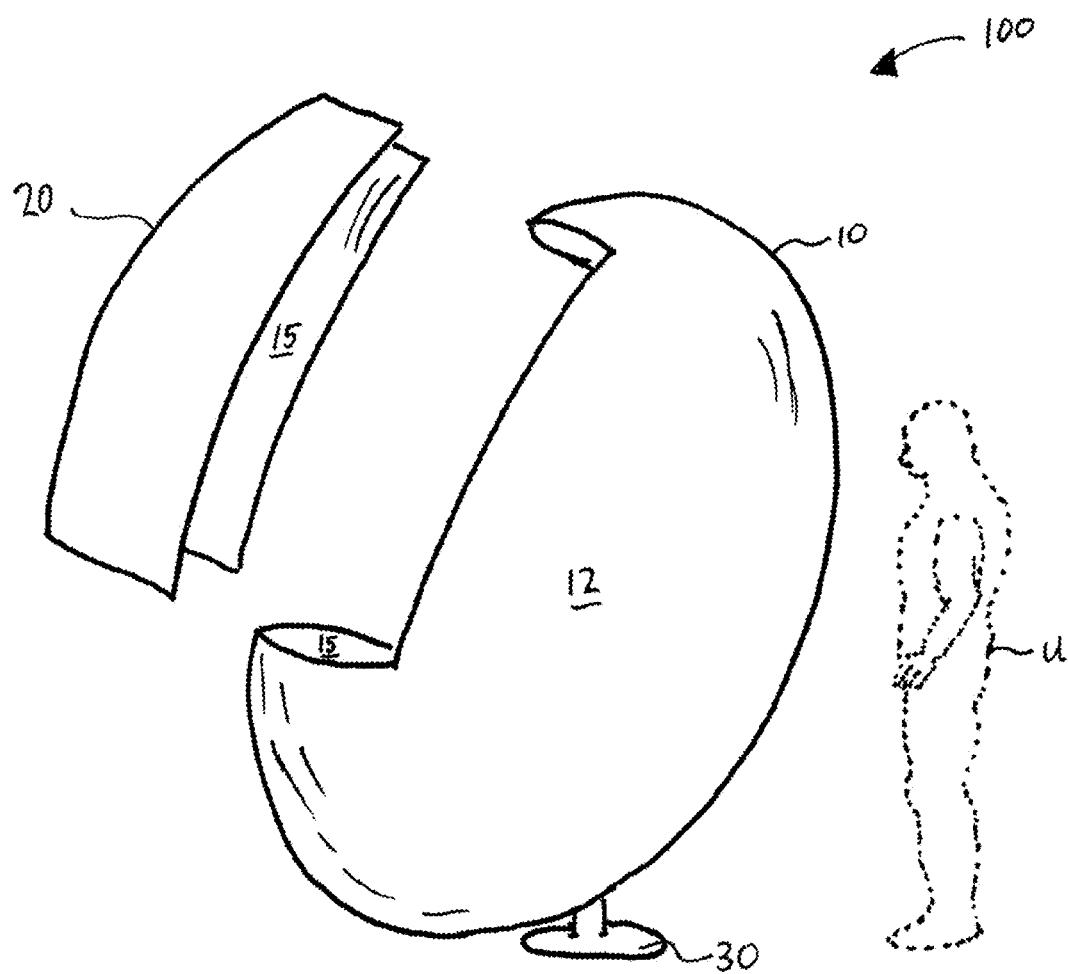
FIG. 3 shows a perspective exploded view of a convertible entertainment pod consistent with one embodiment of the present disclosure.
Figure 4:
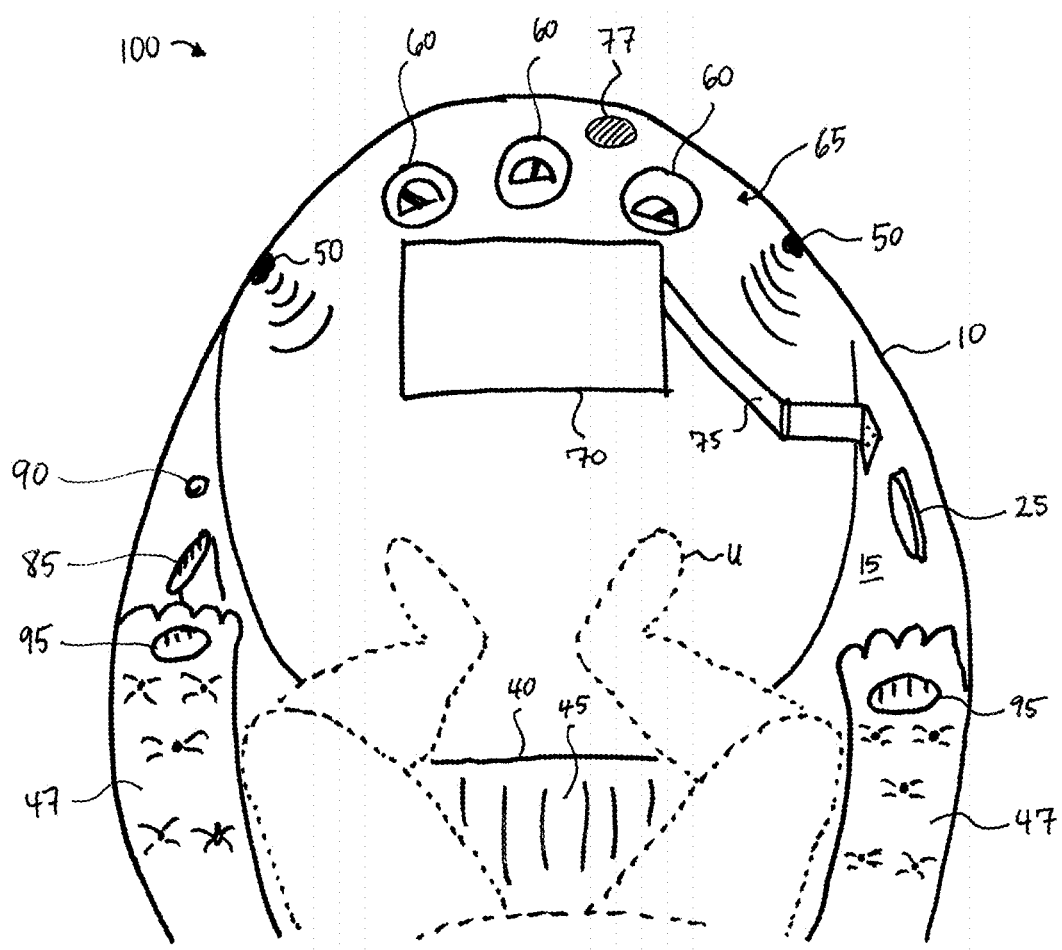
FIG. 4 shows a perspective interior view of a portion of a convertible entertainment pod consistent with one embodiment of the present disclosure.
Figure 5:
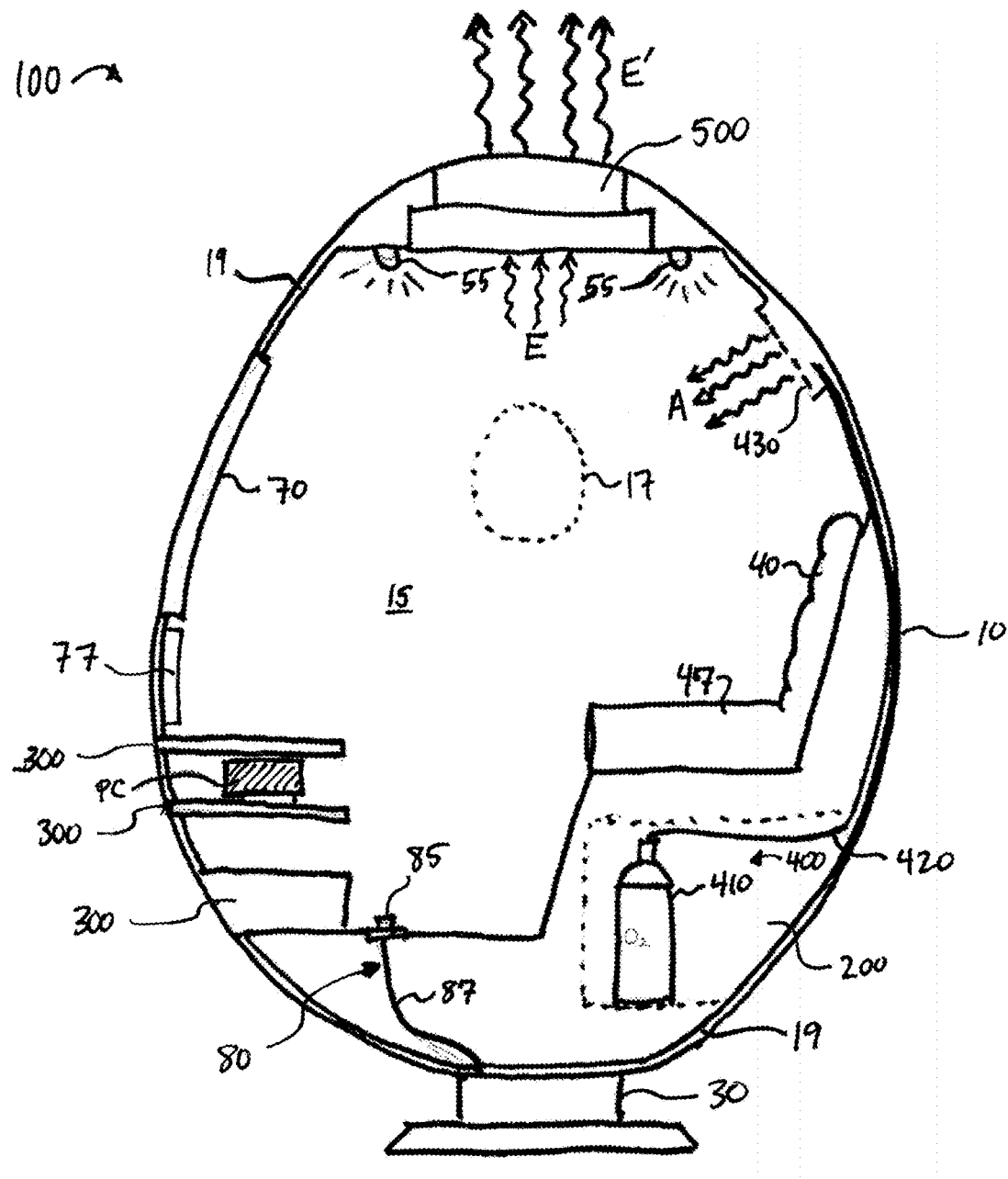
FIG. 5 shows a cutaway view of a convertible entertainment pod consistent with one embodiment of the present disclosure.
Figure 6:
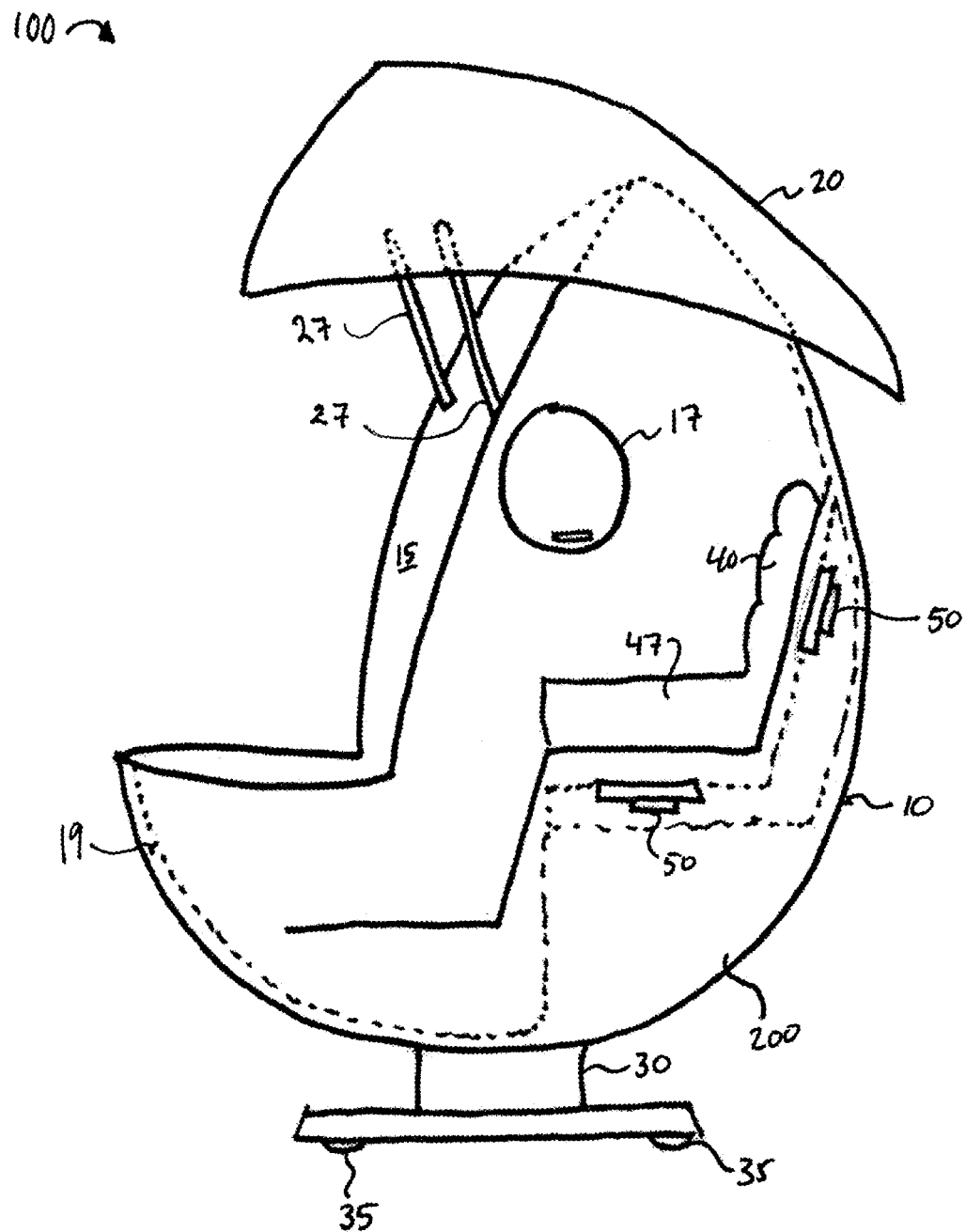
FIG. 6 shows a perspective view of a convertible entertainment pod consistent with one embodiment of the present disclosure.
Figure 7:
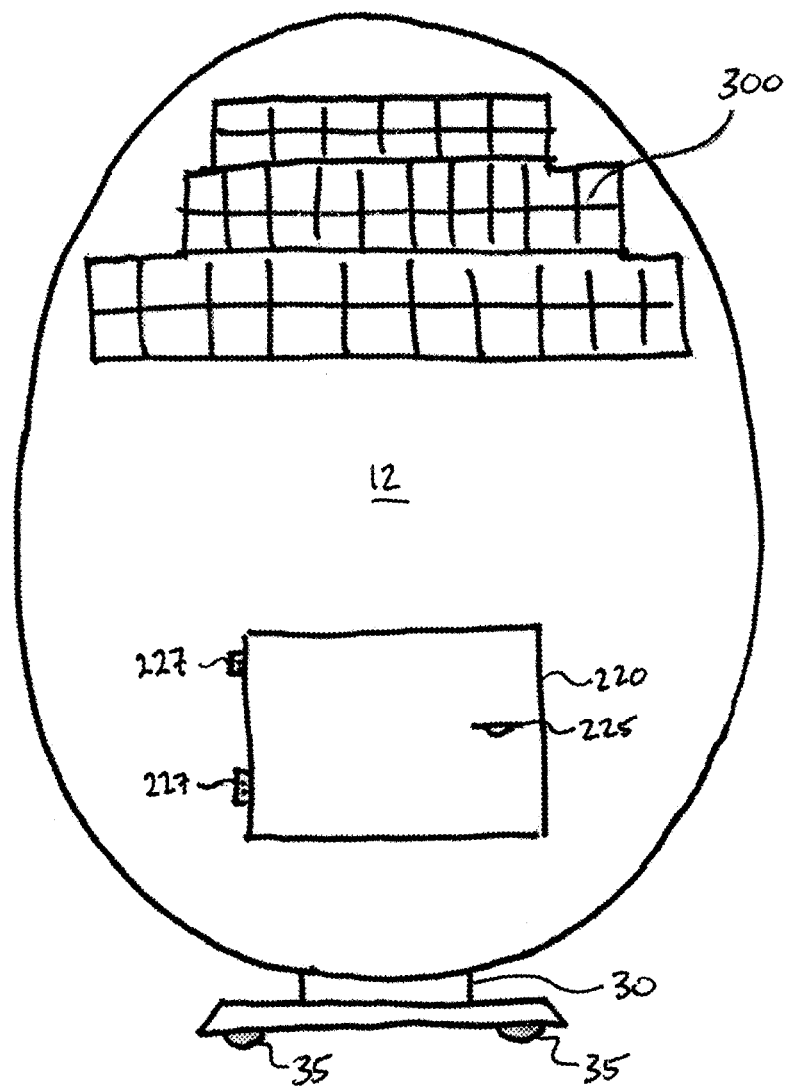
FIG. 7 shows a perspective view of a convertible entertainment pod consistent with one embodiment of the present disclosure.
Figure 8:
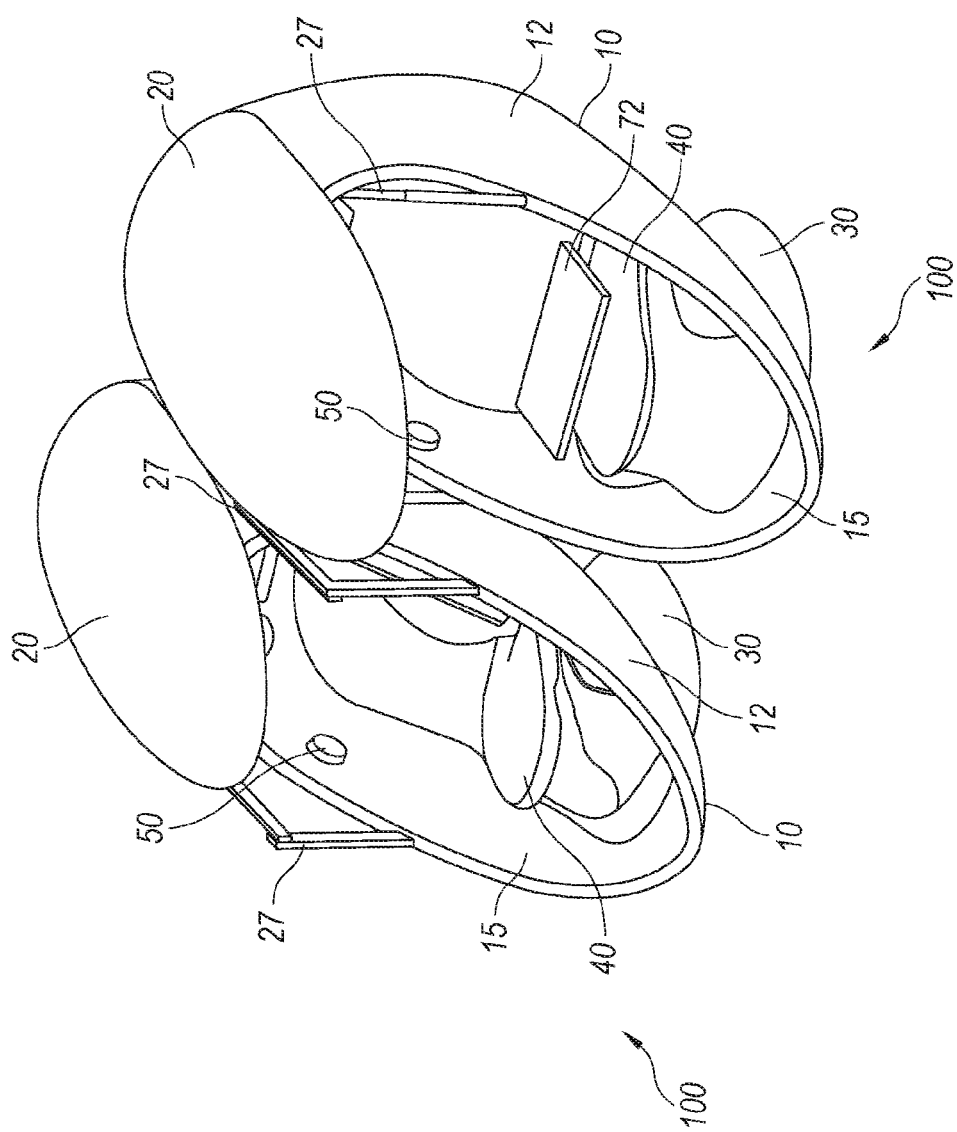
FIG. 8 shows a three-dimensional perspective view of two embodiments of a convertible entertainment pod consistent with multiple embodiments of the present disclosure.
Figure 9:
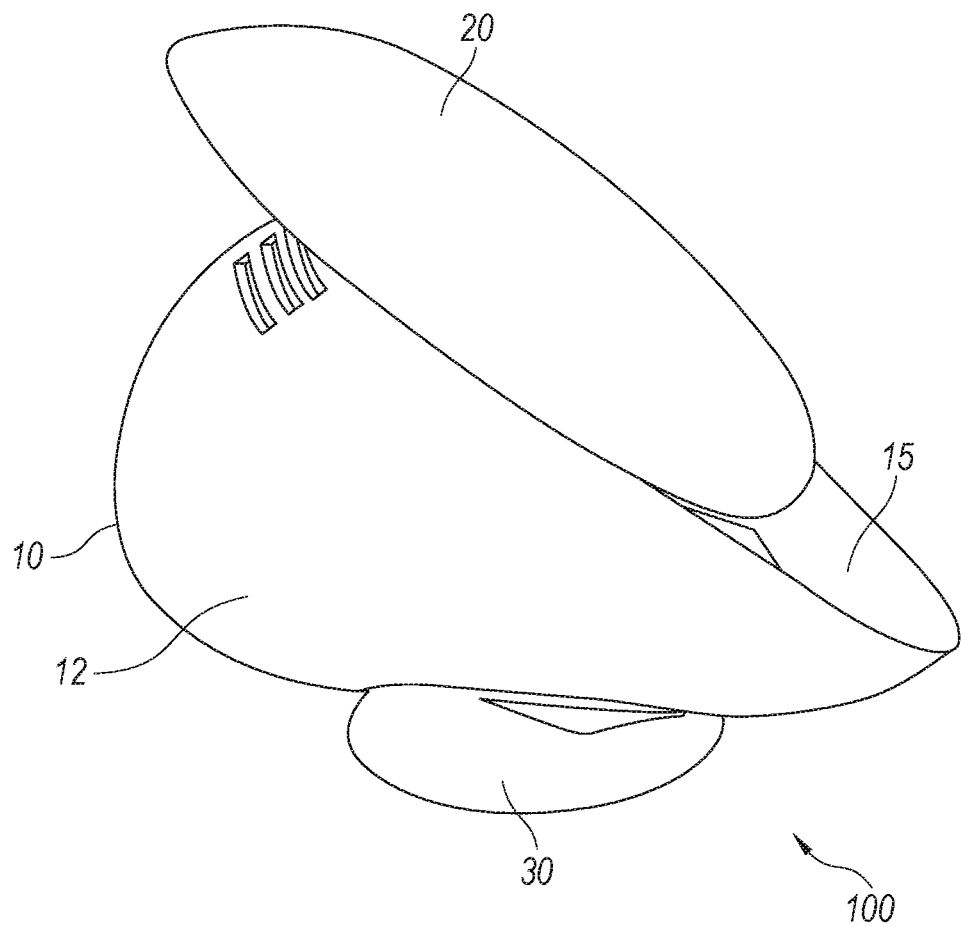
FIG. 9 shows a three-dimensional perspective view of a convertible entertainment pod consistent with one embodiment of the present disclosure.
Figure 10:
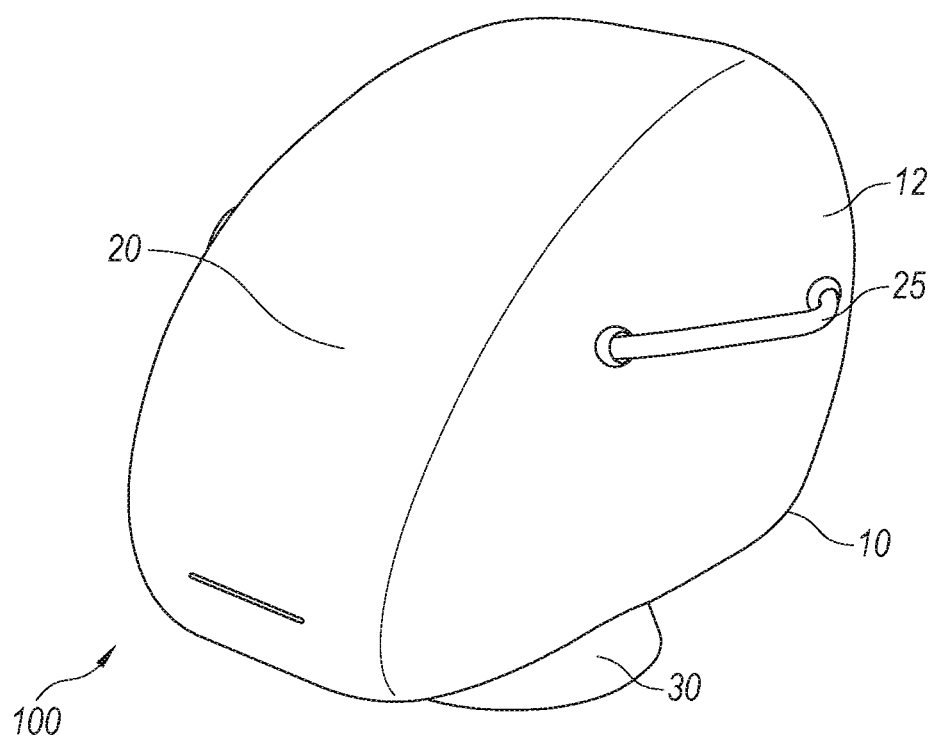
FIG. 10 shows a three-dimensional perspective view of a convertible entertainment pod consistent with one embodiment of the present disclosure.
Figure 11:
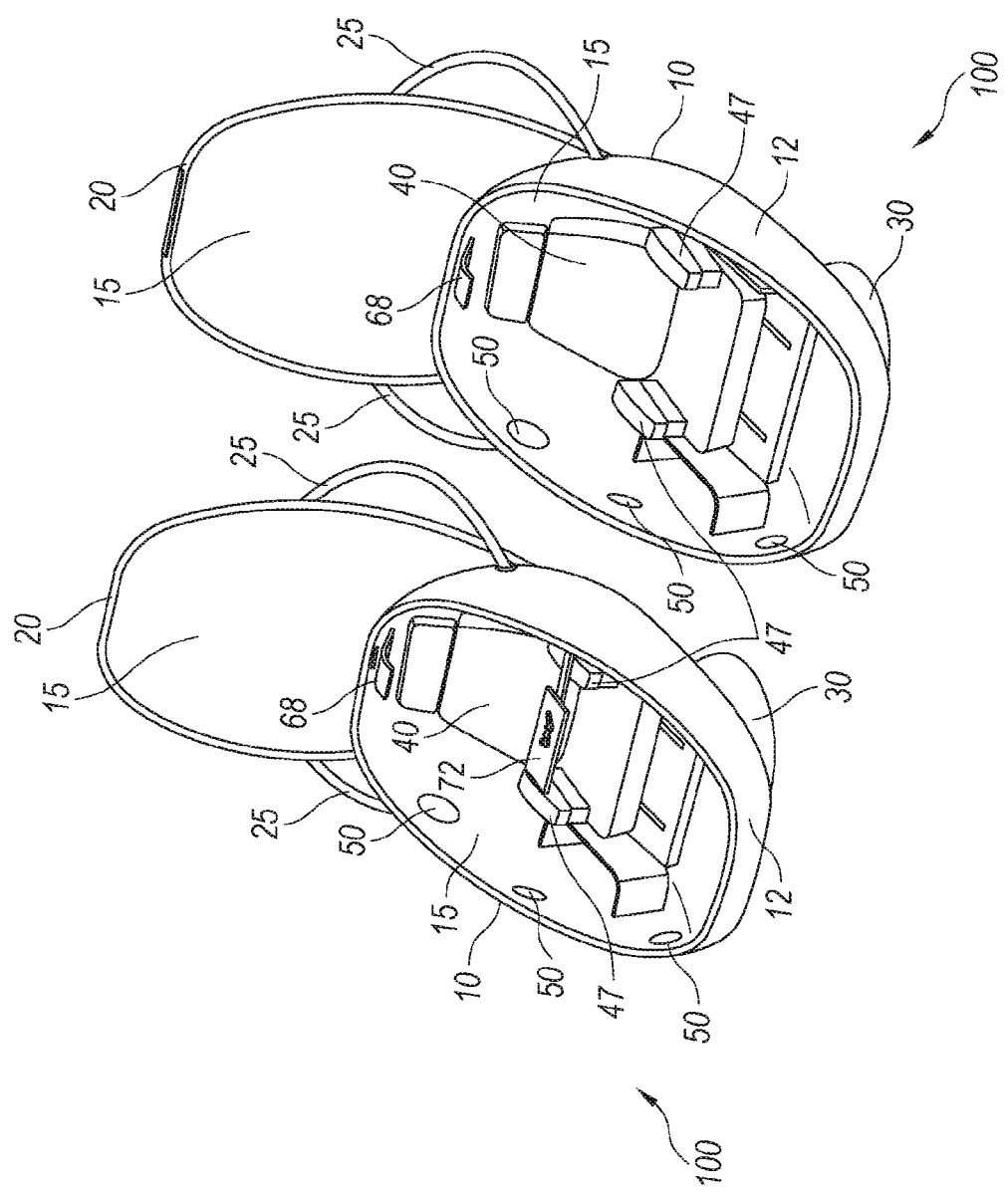
FIG. 11 shows a three-dimensional perspective view of two embodiments of a convertible entertainment pod consistent with multiple embodiment of the present disclosure.
Figure 12:
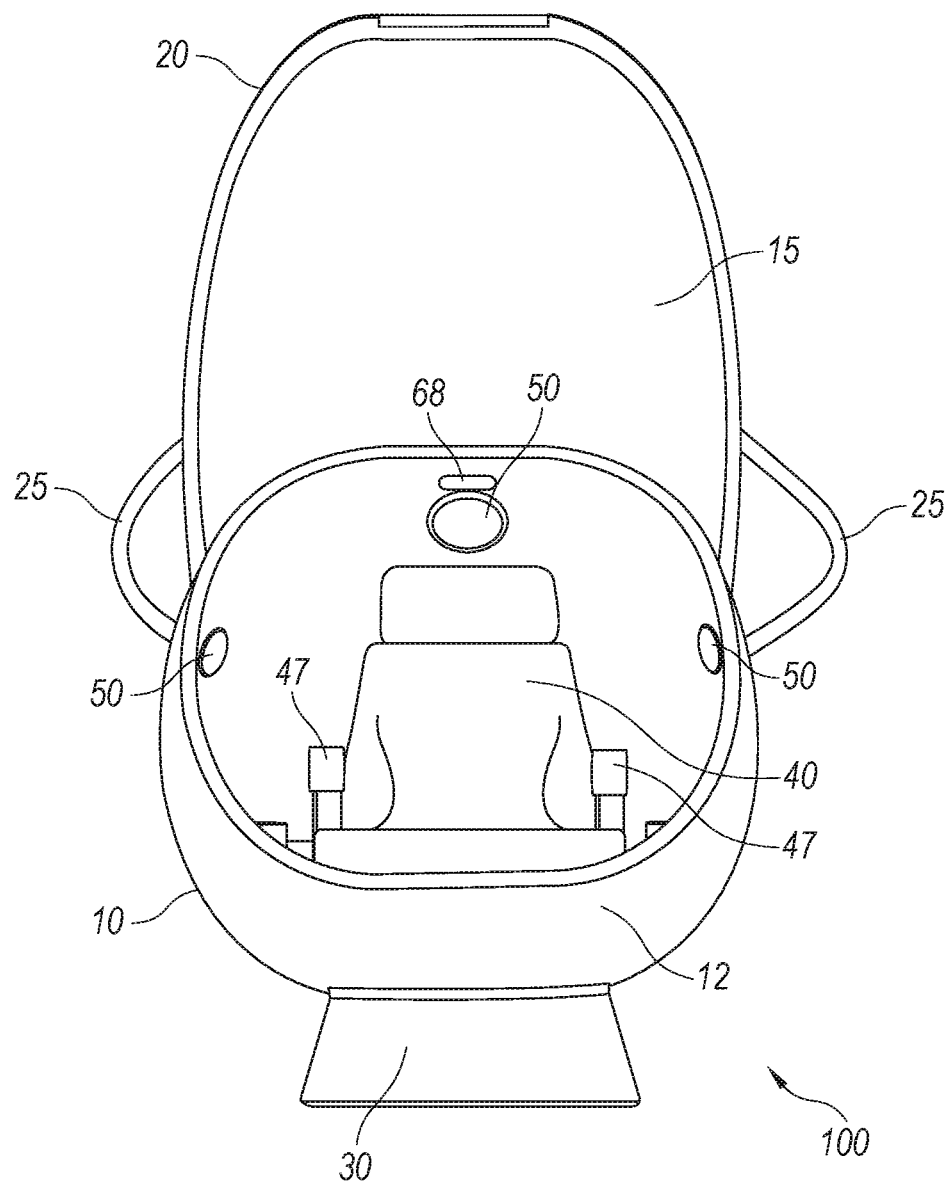
FIG. 12 shows a three-dimensional perspective view of a convertible entertainment pod consistent with one embodiment of the present disclosure.
Figure 13:
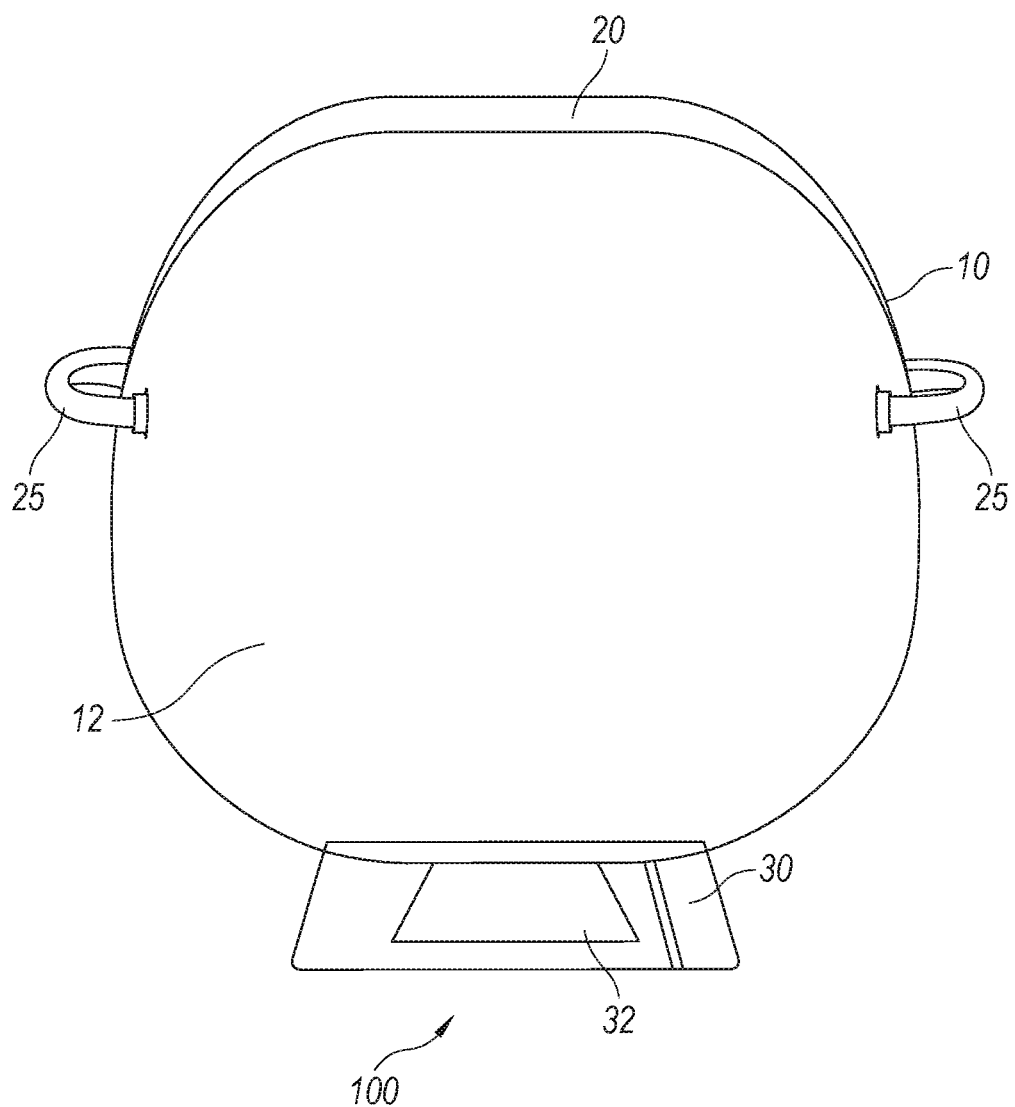
FIG. 13 shows a three-dimensional perspective view of a convertible entertainment pod consistent with one embodiment of the present disclosure.
Figure 14:
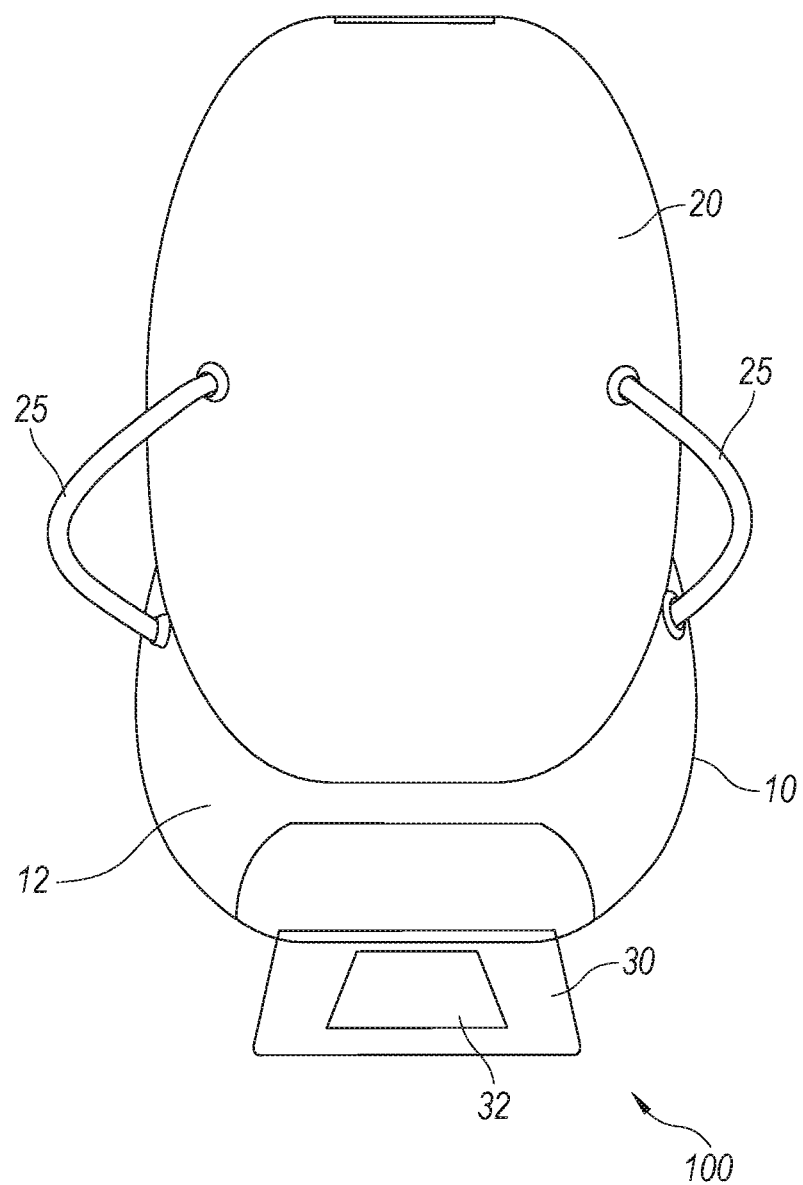
FIG. 14 shows a three-dimensional perspective view of a convertible entertainment pod consistent with one embodiment of the present disclosure.
Figure 15:
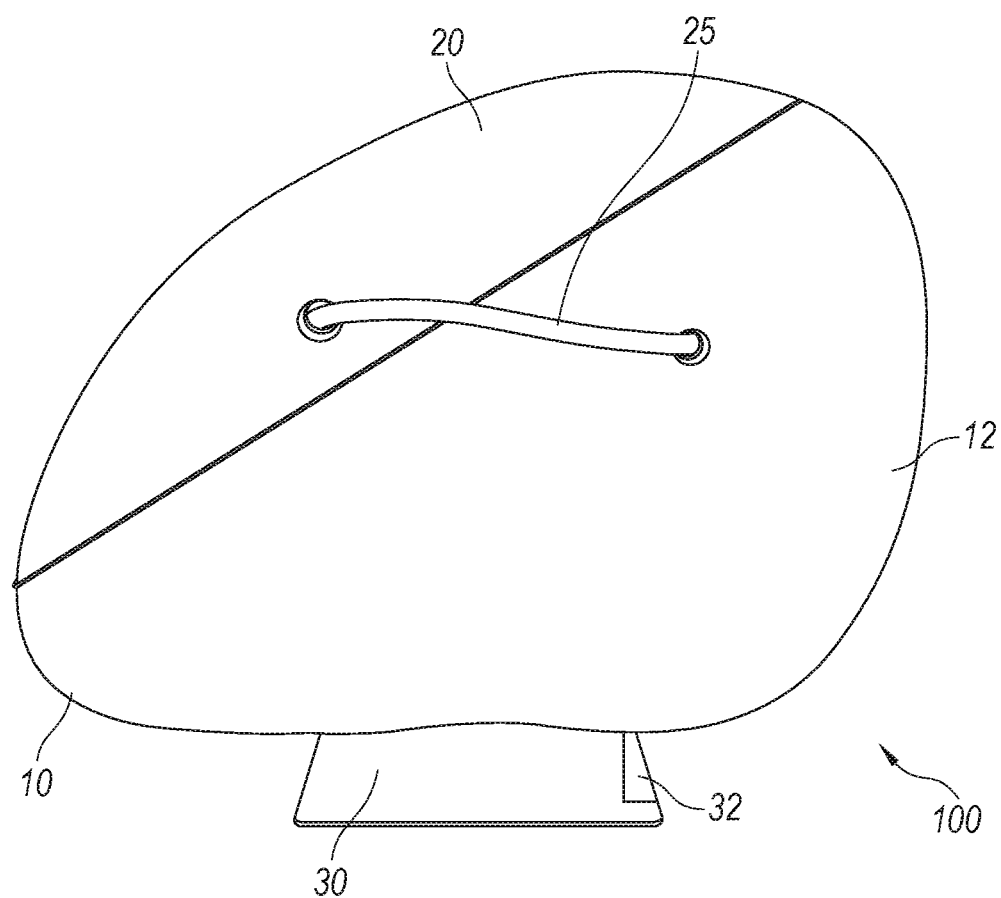
FIG. 15 shows a three-dimensional perspective view of a convertible entertainment pod consistent with one embodiment of the present disclosure.
Figure 16:
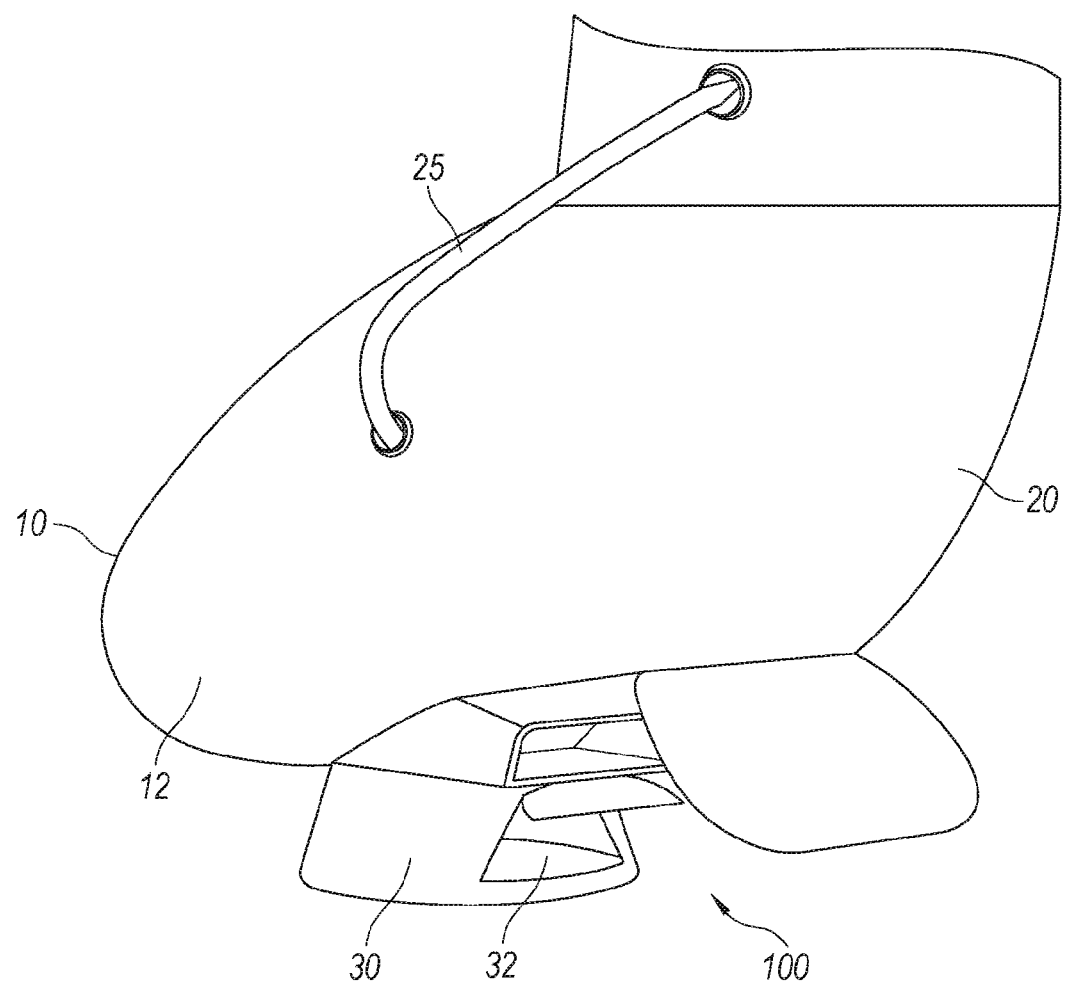
FIG. 16 shows a three-dimensional perspective view of a convertible entertainment pod consistent with one embodiment of the present disclosure.
Figure 17:
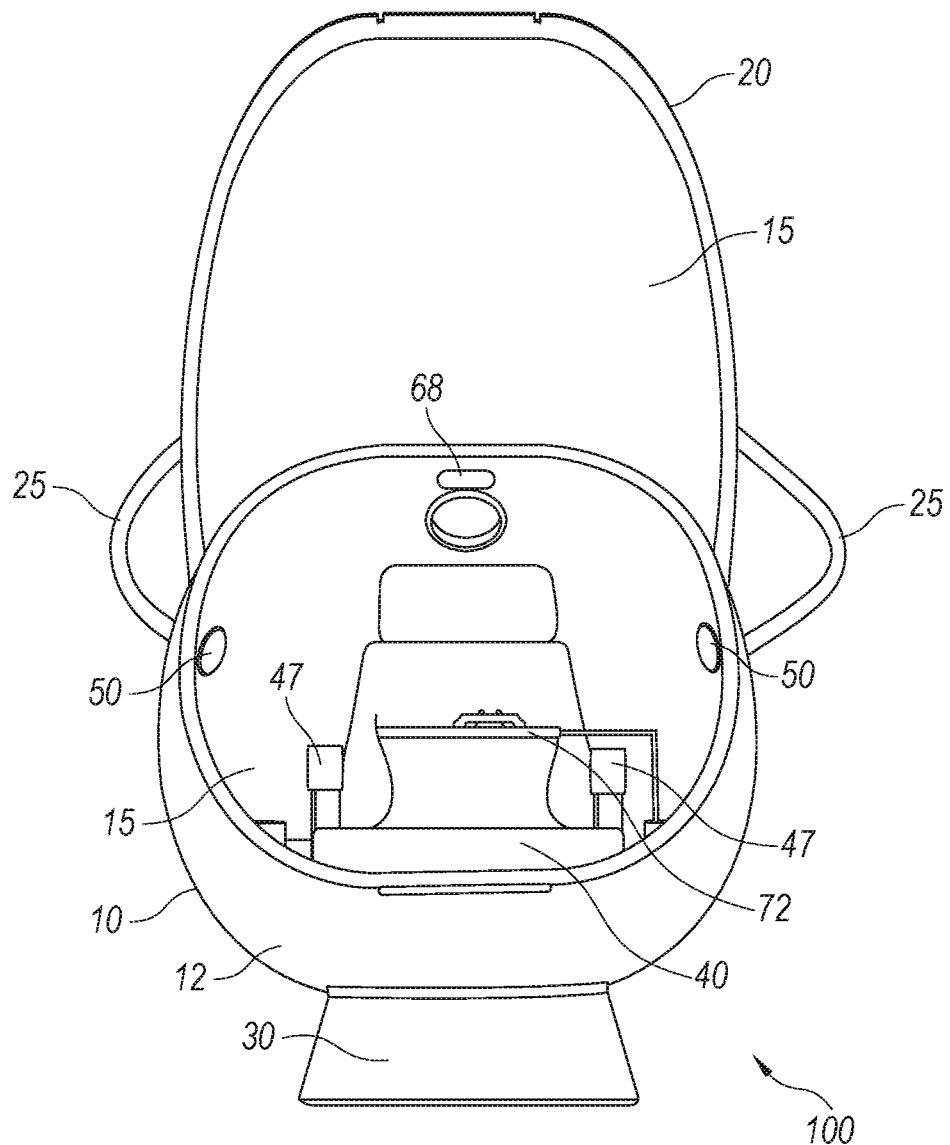
FIG. 17 shows a three-dimensional perspective view of a convertible entertainment pod consistent with one embodiment of the present disclosure.
Figure 18:
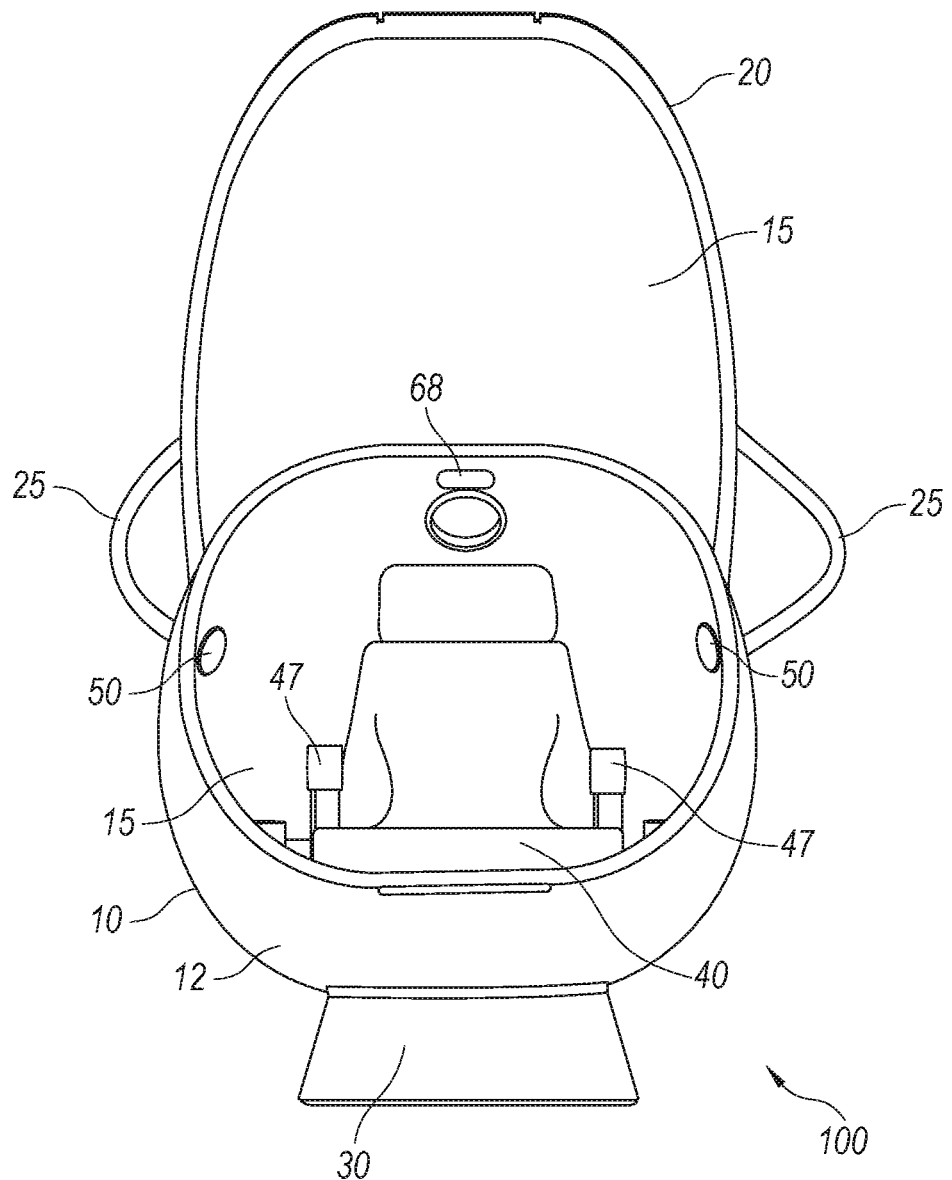
FIG. 18 shows a three-dimensional perspective view of a convertible entertainment pod consistent with one embodiment of the present disclosure.
Figure 19:
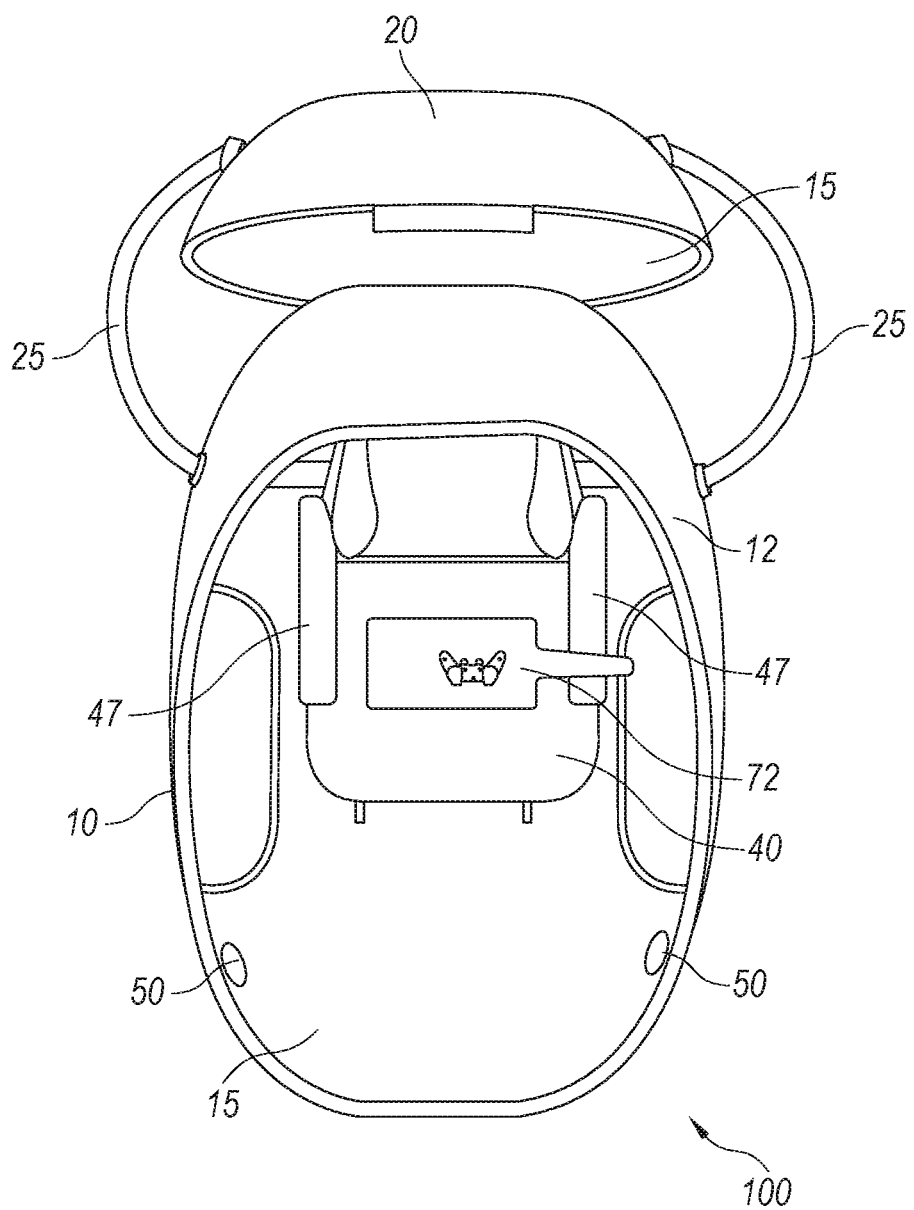
FIG. 19 shows a three-dimensional perspective view of a convertible entertainment pod consistent with one embodiment of the present disclosure.
Figure 20:
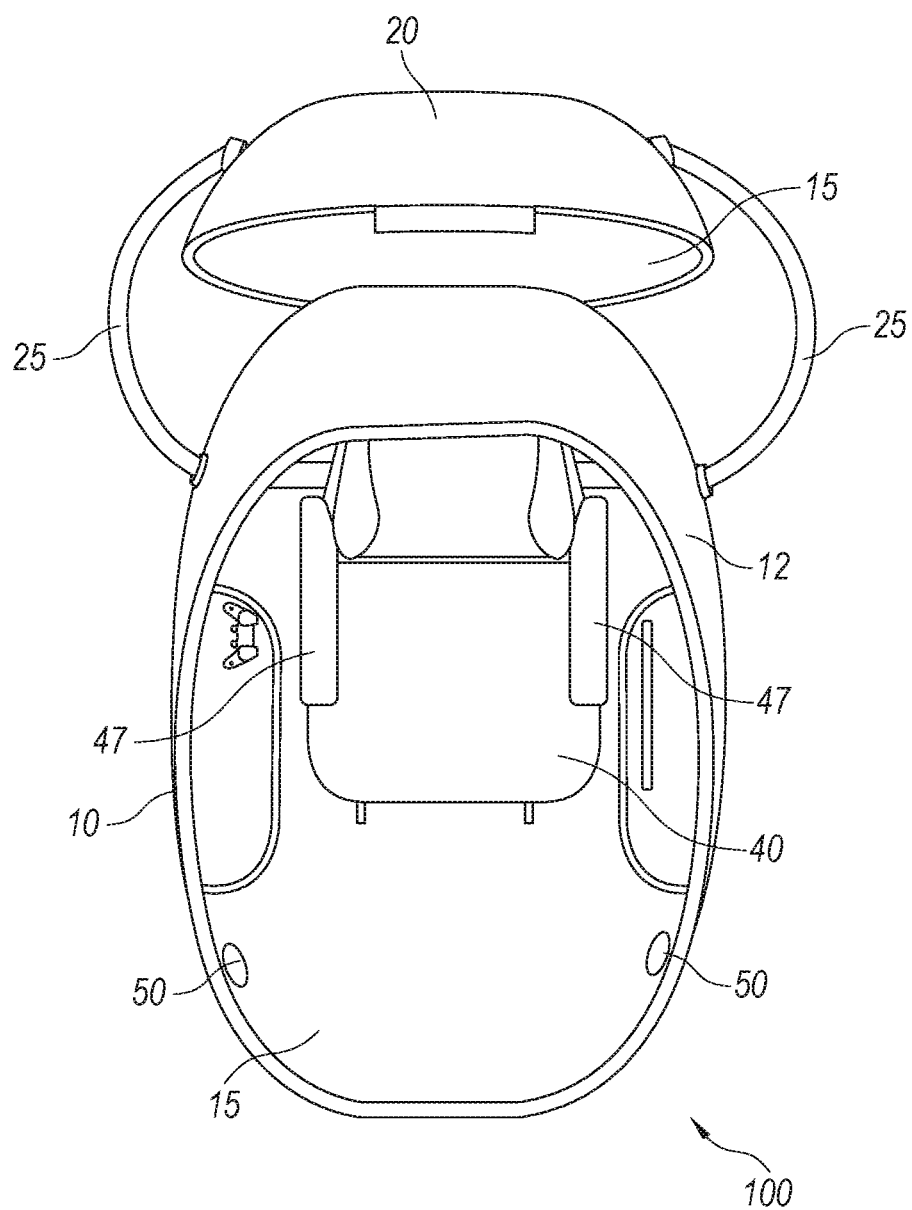
FIG. 20 shows a three-dimensional perspective view of a convertible entertainment pod consistent with one embodiment of the present disclosure.

Referring generally to FIGS. 1-20, the present disclosure provides convertible entertainment pods 100 comprising a shell 10 and a base 30 rotatably associated with the shell 10. The convertible entertainment pods 100 of the present disclosure are sized to comfortably fit at least one person, optionally two people or more than two people. A variety of audio and/or visual devices may be incorporated into the convertible entertainment pods 100, and in some embodiments a user U can customize or modify a particular combination of audio and/or visual devices for inclusion.

The shell 10 may be formed of any suitable material and may be formed into any suitable shape. In some embodiments, the shell 10 is formed of a pliable material, such as a metal or metal alloy. In other embodiments, the shell 10 is formed of a moldable material, such as a resin. In some embodiments, the shell 10 is formed of a carvable material such as wood. In some embodiments, the shell 10 comprises more than one type of material, such as a resin and a metal or metal alloy. Depending on the type of material(s) used, the shell 10 may be formed by, for example, molding (e.g., injection molding), casting, stretching, rolling, braking, joining, carving, welding, fusing, or any combination thereof.

In some embodiments, the shell 10 comprises an insulating layer 19 to insulate the interior portion of the pod 100. The insulating layer 19 can include an acoustical insulating layer for increasing a decibel differential between the interior portion of the pod 100 and the exterior portion of the pod 100. The insulating layer 19 can include a thermal insulation of the exterior portion of the pod 100 from the interior portion of the pod 100. The insulating layer 19 can include space or channels for housing electrical wiring, air ducts, and the like.

In some embodiments, the shell 10 comprises a door 20. In some embodiments, the door is a hinged door, such that opening the door 20 includes rotating the door 20 about the hinge(s). In other embodiments, such as that shown in FIG. 2, the door 20 opens by sliding into a channel or space in the shell 10. In some embodiments, the door 20 opens by sliding into an interior space of the pod 100. In some embodiments, the door 20 includes a handle 25. In some embodiments, the open door position permits the user U to interact freely with guests outside of the pod 100, for example by watching a television in the room while sitting in the pod 100. In some embodiments, the door 20 is hinged along one side of the door 20. In some embodiments, the door 20 is hinged along the top edge, such that opening the door 20 comprises lifting the door 20. In such embodiments, the door 20 may further comprise one or more struts 27 (e.g., pressurized strut(s)) for reducing the amount of lifting force required and/or for enabling the door 20 to remain in an open position until a user U causes the door 20 to close. In some embodiments, the door 20 comprises a latch for securing the door 20 in a closed position. In some embodiments, the latch may be released by a pull or similar latch release mechanism. In some embodiments, the door 20 is in functional communication with a motor, such that opening and closing the door 20 comprises activating the motor. In some embodiments, the door 20 does not include a latch.

In some embodiments, the shell 10 comprises a window 17. The window 17 may be incorporated into any portion(s) of the shell 10. In some embodiments, the window 17 may be covered or partially covered to reduce the amount of ambient light entering the pod 100 and/or the amount of light and/or sound emanating from the pod 100.

The shell 10 comprises an inner surface 15 and an outer surface 12. In some embodiments, the outer surface 12 includes a texture, a design, a pattern, or a combination thereof. In some embodiments, the outer surface 12 can be easily customized by a user, for example by application of a customized skin. In some embodiments, the outer surface 12 comprises a solar panel 300. In some embodiments, the solar panel 300 provides enough power to operate at least a portion of the electrical components of the pod 100, such as lights 55, ventilation 400, control units 65, and/or audio/video components PC.

In some embodiments, the inner surface 15 includes a texture. In some embodiments, the texture reduces an echo effect, such as a reverberation effect, of sound provided to the interior portion of the pod 100. In some embodiments, the inner surface 15 includes a pocket 85 for storing small objects, such as a remote control or mobile phone.

In some embodiments, the base 30 includes one or more wheels 35 for enabling the pod 100 to be moved. In some embodiments, the wheels 35 may be lockable, for example to prevent movement of the pod 100 after it has been placed in a desired location. In some embodiments, the wheels 35 automatically lock when a weight above a threshold weight is added to the pod 100. In some embodiments, the pod 100 includes a solar panel 300 and one or more wheels 35, such that the pod 100 may be used outdoors using power obtained substantially or exclusively from the solar panel 300. In some embodiments, the base 30 includes a storage compartment 32, which may also contain hardware (electrical components, plugs, amplifier, oxygen system, etc.).

In some embodiments, at least one audio speaker 50 is associated with (e.g., affixed to) the shell 10, such as at the inner surface 15. In some embodiments, the at least one audio speaker 50 includes a subwoofer. In some embodiments, the subwoofer is positioned beneath or behind the seating portion 40. In some embodiments, the at least one audio speaker 50 comprises a plurality of speakers 50 configured to provide surround sound audio to a user U. In some embodiments, the at least one audio speaker comprises a 5/7/12-speaker surround sound configuration driven by a 3D acoustic protocol. In some embodiments, at least one audio speaker 50 is associated with the outer surface 12 such that the speaker can be heard by guests outside of the pod 100. In some embodiments, controls permit the user U to separately control one or more of the audio speakers 50.

In some embodiments, the shell 10 comprises a shelf 300 on the inner surface 15. In some embodiments, the shelf 300 is for securing or docking an audio or video component, such as a gaming system or personal computer PC, to the pod 100. In some embodiments, door 220 is attached to shell 12 by hinges 227. Handle 225 is located on the exterior side and/or the interior side of the door 220 to open such door.

In some embodiments, the inner surface 15 is configured to accommodate virtual or augmented reality systems. In some embodiments, the pod 100 has dimensions suitable to enable a user U to freely stand, sit, lunge, squat, lift arms, kick legs, and/or any combination thereof to interact with the virtual or augmented reality system. In some embodiments, the pod 100 comprises one or more sensors (e.g., motion sensors) for detecting a position and/or movement of a user U or any portion of a user U to enable the user U to interact with the virtual or augmented reality system.

In some embodiments, the pod 100 further includes a seating portion 40. In some embodiments, the seating portion 40 is affixed to the shell 10, for example by securing (e.g., adhering) the seating portion 40 to the inner surface 15 of the shell 10. In other embodiments, the seating portion 40 may be formed from a continuous piece of material as the shell 10, for example by molding the shell 10 and the seating portion 40 in one step. In some embodiments, the seating portion 40 includes a cushion 45, which in some embodiments may be removable. In some embodiments, the seating portion 40 includes one or more armrests 47, which may include a cavity 95 for holding a beverage or other small object. In some embodiments, the seating portion 40 can be positioned in a reclined or flat configuration. In some embodiments, the seating portion 40 includes one or more motors for assisting a user U to adjust the position and/or configuration of the seating portion 40.

In some embodiments, the pod 100 further includes at least one light 55 secured to the inner surface 15 of the shell 10. In some embodiments, the at least one light 55 comprises a sound-activated light. In some embodiments, the at least one light 55 is an LED light, such as a white LED light, a yellow LED light, a green LED light, a red LED light, a blue LED light, a multi-color LED light, and/or a dimmable LED light. In some embodiments, the at least one light 55 comprises a sound-activated multi-color LED light.

In some embodiments, the pod 100 further includes a ventilation system 400. In some embodiments, the ventilation system 400 is incorporated into the shell 10 and recirculates ambient air, provides fresh air, and/or provides a customized atmosphere A to the interior portion of the pod 100. In some embodiments, the ventilation system 400 includes an artificial atmosphere source 410 (e.g., a compressed gas cylinder) connected to one or more outlets 430 by one or more ducts 420. In some embodiments, the ventilation system 400 includes a thermal module for providing the atmosphere A at a desired temperature to the interior portion of the pod 100. In some embodiments, the ventilation system 400 includes an enhanced oxygen source 410 for providing an atmosphere A that has an increased amount of oxygen, compared to the oxygen content of ambient air, to the interior portion of the pod 100. In some embodiments, the ventilation system 400 further includes an exhaust vent 500 for removing unwanted atmosphere E from the inside portion of the pod 100 to the outside portion of the pod 100 in the form of exhaust E'.

In some embodiments, the pod 100 further includes a heating/cooling system that incorporates a heating coil and/or air conditioning system similar to that of a motor vehicle in order to maintain the internal temperature within a comfortable range.

In some embodiments, the pod 100 further comprises a video display 70. In some embodiments, the video display 70 is secured to the pod 100 by a bracket 75, such as an articulating arm. In some embodiments, the video display 70 is incorporated into the inner surface 15 of the shell 10, for example into the inner surface 15 of the door 20. In some embodiments, the video display 70 is a curved display, optionally wherein at least a portion of the inner surface 15 of the shell includes a contour that is complementary to the curvature of the curved display 70.

In some embodiments, the pod 100 further comprises a video projector 68. Images from the video projector 68 may be projected onto a screen within the pod 100, and/or onto the inner surface 15 of the shell 10. In some embodiments, the inner surface 15 is a passive screen or surface inside door 20 onto which images can be projected by projector 68.

In some embodiments, a tray table 72 is attached to the interior of the pod above the seating portion 40. In some embodiments, tray table 72 is adjustable to the user's required height and location within the pod.

In some embodiments, the pod 100 includes a control unit 65 for enabling a use U to adjust one or more settings of the pod 100. For example, the control unit 65 may include one or more control displays 60 (e.g., gauges, displays, meters, or indicator lights) corresponding to one or more conditions of the pod 100, such as the internal ambient temperature, the intensity and/or hue of interior lighting, power status of the ventilation system, ambient oxygen level inside the pod 100, volume of sound inside the pod 100, volume of sound outside the pod 100, etc. In some embodiments, the control unit 65 comprises a touch screen with a graphical user interface (GUI) for enabling control of any adjustable feature of the pod 100.

In some embodiments, the pod 100 includes at least one jack 90 for receiving or distributing a video or audio signal. For example and without limitation, the at least one jack 90 may be an HDMI port, a USB port, an Ethernet port, an RCA port, a VGA port, a coaxial port, a stereo jack (e.g., ¼" or ⅛"), a mono jack (e.g., ¼" or ⅛"), or an optical port. In some embodiments, one or more jacks 19 are located in close proximity to each other. In some embodiments, the at least one jack 19 is provided such that the jack opening is flush or substantially flush with the inner surface 15 of the shell 10. In some embodiments, the at least one jack 19 is connected to an audio or visual output device, such as the display 70 and/or the at least one speaker 50. In other embodiments, the at least one jack 19 is in electronic communication with the control unit 65.

In some embodiments, the pod 100 includes one or more ports 19 or wireless connectivity devices for electronically connecting to a computer, such as a personal computer. In some embodiments, the one or more ports 19 includes a VGA, RGA, HDMI, USB, serial, or other computer-compatible port.

In some embodiments, the pod 100 includes one or more ports 19 or wireless connectivity devices for enabling communication between the pod 100 and audio/visual input devices and/or between the pod 100 and data transmitters/receivers. For example and without limitation, the pod 100 may include one or more Ethernet ports and/or hardware for enabling data to pass to and from the pod 100. Similarly, the pod 100 may include (e.g., may additionally include) a wireless receiver and/or transmitter for enabling data to pass to wirelessly and from the pod 100, for example using a Bluetooth or WiFi (e.g., IEEE 802.11) protocol. In some embodiments, the pod 100 includes HDMI, USB, radio wave, telephone, coaxial, and/or other connectivity capabilities.

In some embodiments, the pod 100 includes a control 80 for selectably enabling and preventing rotational freedom of the pod 100 relative to the base 30. In some embodiments, the control 80 includes a lever 85 operably connected to the base 30, for example by one or more cables 87. In some embodiments, the control 80 includes a switch or lever 85 in the interior portion of the pod 100 so that it is accessible to a user while the door 20 is closed. In other embodiments, the control 80 automatically prevents rotation of the pod 100 relative to the base 30 when the door 20 is closed. In some embodiments, the control 80 automatically prevents rotation of the pod 100 relative to the base 30 when a weight above a threshold weight is added to the pod 100.

In some embodiments, the pod 100 comprises active noise cancellation for reducing a decibel level outside the pod 100. In some embodiments, a sound level outside the pod 100 is at least about 40 dB lower than the decibel level inside the pod 100, for example at least 40 dB, at least 50 dB, at least 60 dB, at least 70 dB, at least 80 dB, or at least 90 dB less than the decibel level inside the pod 100. In some embodiments, the active noise cancellation produces random noise interference, for example according to U.S. Pat. Nos. 2,866,848, 2,920,138, and/or 2,966,549, the entire contents of each of which are incorporated herein by reference.

In some embodiments, the present disclosure provides a convertible entertainment pod comprising a shell comprising an inner surface, an outer surface, and a closeable door; a base rotatably affixed to the outside surface of the shell; and a seating portion affixed to or integrated into the inner surface of the shell, wherein the convertible entertainment pod adopts a first, enclosed configuration when the closeable door is in a closed position. In some embodiments, the convertible entertainment pod adopts a second, unenclosed configuration when the door is in an open position. In some embodiments, the convertible entertainment pod further comprises at least one audio speaker providing an audio signal from the inner surface of the shell. In some embodiments, the audio signal has a first decibel level observable from outside the convertible entertainment pod when the convertible entertainment pod is in the first, enclosed configuration, and a second decibel level observable from outside the convertible entertainment pod when the convertible entertainment pod is in the second, unenclosed configuration, and wherein the first decibel level is significantly less than the second decibel level. In some embodiments, the first decibel level is at least 40 dB less than the second decibel level, optionally wherein the first decibel level is at least 50 dB, at least 60 dB, at least 70 dB, at least 80 dB, or at least 90 dB, at least dB less than the second decibel level. In some embodiments, the at least one audio speaker comprises a subwoofer, optionally positioned between the inner surface of the shell and the seating portion. In some embodiments, the convertible entertainment pod further comprises an insulating layer associated with the shell. In some embodiments, the convertible entertainment pod of any preceding claim further comprises a ventilation system incorporated in the shell. In some embodiments, the ventilation system comprises an enhanced oxygen source for providing an atmosphere inside the convertible entertainment pod having a level of oxygen that is greater than a level of oxygen in an atmosphere outside the convertible entertainment pod. In some embodiments, the convertible entertainment pod further comprises at least one light associated with the inner surface of the shell. In some embodiments, the at least one light comprises sound-activated multi-color LED lighting. In some embodiments, the convertible entertainment pod further comprises at least one of: a video display, a video camera, a virtual reality system, and augmented reality system. In some embodiments, the video display is a curved display. In some embodiments, at least a portion of the inner surface of the shell conforms to the curved video display. In some embodiments, the convertible entertainment pod further comprises a window incorporated within the shell. In some embodiments, the convertible entertainment pod further comprises at least one input jack for connecting a video or audio device to the convertible entertainment pod. In some embodiments, the convertible entertainment pod is capable of wirelessly connecting with one or more additional devices via a wireless connectivity protocol. In some embodiments, the one or more additional devices comprises a second convertible entertainment pod. In some embodiments, the wireless connectivity protocol comprises a Bluetooth protocol. In some embodiments, the convertible entertainment pod further comprises a control panel for adjusting one or more components of the convertible entertainment pod. In some embodiments, the control panel comprises a graphical user interface. In some embodiments, the inner surface of the shell comprises a texture. In some embodiments, the texture reduces echo and/or reverberation of an audio signal provided within the convertible entertainment pod. In some embodiments, the inner surface of the shell comprises at least one shelf. In some embodiments, the seat portion is adjustable and/or replaceable. In some embodiments, the convertible entertainment pod further comprises at least one seating cushion. In some embodiments, the convertible entertainment pod further comprises a control for selectably enabling and preventing rotational freedom of the shell relative to the stand. In some embodiments, the control for selectably enabling and preventing rotational freedom is accessible to a user within the convertible entertainment pod while the convertible entertainment pod is in a first, enclosed configuration. In some embodiments, the control for selectably enabling and preventing rotational freedom prevents a user within the convertible entertainment pod from enabling rotational freedom while the convertible entertainment pod is in a first, enclosed configuration. In some embodiments, the convertible entertainment pod further comprises a solar panel for providing electrical power to at least one electrical feature or component associated with the pod.

While the technology disclosed herein is capable of being embodied in various forms, the several embodiments are described with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." Also, the disclosure of ranges is intended as a continuous range including every value between the minimum and maximum values recited as well as any ranges that can be formed by such values. Also disclosed herein are any and all ratios (and ranges of any such ratios) that can be formed by dividing a disclosed numeric value into any other disclosed numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

From the foregoing, it will be appreciated that specific embodiments of the invention have been described herein for purposes of illustration, but that various modifications may be made without deviating from the scope of the invention. Accordingly, the invention is not limited except as by the appended claims.

In some embodiments, the pod 100 can be used for listening to music. In some embodiments, the pod 100 can be used for watching television and movies. In some embodiments, the pod 100 can be used for streaming content. In some embodiments, the pod 100 can be used for gaming or interacting with virtual reality and augmented reality systems.

In some embodiments, pod 100 can be used as a private environment for mobile computing. In some embodiments, pod 100 can be used as a private environment for video/conference calls. In some embodiments, pod 100 includes a microphone to better enable video/conference calls. In some embodiments, pod 100 can be used as a private environment for software training modules for a professional work environment.

In some embodiments, pod 100 may have application in therapeutic use as an enclosed chamber for meditation and treatment, such as aromatherapy, light therapy, oxygen therapy, etc. This embodiment may be used as alternative therapy for stress, anxiety, and other disorders.

In some embodiments, pod 100 can provide a quiet place for sleep purposes with a comfortable chair that reclines in which the user can nap. Active noise cancellation discussed herein allows for complete isolation in some embodiments.

In some embodiments, pod 100 can be used for social interacting via video chatting. In some embodiments, pod 100 can be used for social interacting via multiplayer gaming systems. In some embodiments, pod 100 can be used for social interacting via eSports broadcasts.

In some embodiments, pod 100 can integrate and control a user's home control devices such as thermostats, security systems, lighting, etc.

In some embodiments, pod 100 has educational applications. In some embodiments, pod 100 can be used to conduct training modules. In some embodiments, pod 100 can be used to conduct flight simulations. In some embodiments, pod 100 can be used to conduct educational material.

In some embodiments, pod 100 can be used in athletics, or otherwise, for watching game tape. In some embodiments, pod 100 can be used in athletics, or otherwise, for conducting visualization exercises. In some embodiments, pod 100 can be used in athletics, or otherwise, for conducting motivational exercises. In some embodiments, pod 100 can be used in athletics, or otherwise, for watching footage of past or live games or events.

In some embodiments, pod 100 has commercial uses such as sleep clubs, for example, by-hour rentals in public locations. Shopping malls, airports, and movie theaters are just some examples of other public locations where pod 100 can be located for short term (e.g., rental) use by a member of the public.

In some embodiments, the pod 100 is able to provide noise cancellation. Noise cancellation allows sounds from a person's environment to be diminished or entirely eliminated during work or relaxation. Such sounds interfere with a person's ability to experience silence or other desired audio sounds. Other approaches to this problem include "sound masking," in which white or pink noise is introduced to cover external sounds from the environment. Noise cancellation can be active or passive. Active noise cancellation requires the use of a power source. Passive noise cancellation includes the use of materials that absorb and block sound. The disclosure herein includes active noise cancellation.

EXAMPLES

Example 1

A convertible entertainment pod comprising:
a shell comprising an inner surface, an outer surface, and a closeable door;
a base rotatably affixed to the outside surface of the shell; and
a seating portion affixed to or integrated into the inner surface of the shell,
wherein the convertible entertainment pod adopts a first, enclosed configuration when the closeable door is in a closed position.

Example 2

The convertible entertainment pod of Example 1, wherein the convertible entertainment pod adopts a second, unenclosed configuration when the door is in an open position.

Example 3

The convertible entertainment pod of Example 1 or Example 2 further comprising at least one audio speaker providing an audio signal from the inner surface of the shell.

Example 4

The convertible entertainment pod of Example 4, wherein the audio signal has a first decibel level observable from outside the convertible entertainment pod when the convertible entertainment pod is in the first, enclosed configuration, and a second decibel level observable from outside the convertible entertainment pod when the convertible entertainment pod is in the second, unenclosed configuration, and wherein the first decibel level is significantly less than the second decibel level.

Example 5

The convertible entertainment pod of Example 4, wherein the first decibel level is at least 40 dB less than the second decibel level, optionally wherein the first decibel level is at least 50 dB, at least 60 dB, at least 70 dB, at least 80 dB, or at least 90 dB less than the second decibel level.

Example 6

The convertible entertainment pod of any one of Examples 3 to 5, wherein the at least one audio speaker comprises a subwoofer, optionally positioned between the inner surface of the shell and the seating portion.

Example 7

The convertible entertainment pod of any preceding Example further comprising an insulating layer associated with the shell.

Example 8

The convertible entertainment pod of any preceding Example further comprising a ventilation system incorporated in the shell.

Example 9

The convertible entertainment pod of Example 8, wherein the ventilation system comprises an enhanced oxygen source for providing an atmosphere inside the convertible entertainment pod having a level of oxygen that is greater than a level of oxygen in an atmosphere outside the convertible entertainment pod.

Example 10

The convertible entertainment pod of any preceding Example further comprising at least one light associated with the inner surface of the shell.

Example 11

The convertible entertainment pod of Example 10, wherein the at least one light comprises sound-activated multi-color LED lighting.

Example 12

The convertible entertainment pod of any preceding Example further comprising at least one of: a video display, a video camera, a virtual reality system, and augmented reality system.

Example 13

The convertible entertainment pod of Example 12, wherein the video display is a curved display.

Example 14

The convertible entertainment pod of Example 13, wherein at least a portion of the inner surface of the shell conforms to the curved video display.

Example 15

The convertible entertainment pod of any preceding Example further comprising a window incorporated within the shell.

Example 16

The convertible entertainment pod of any preceding Example further comprising at least one input jack for connecting a video or audio device to the convertible entertainment pod.

Example 17

The convertible entertainment pod of any preceding Example, wherein the convertible entertainment pod is capable of wirelessly connecting with one or more additional devices via a wireless connectivity protocol.

Example 18

The convertible entertainment pod of Example 17, wherein the one or more additional devices comprises a second convertible entertainment pod.

Example 19 The convertible entertainment pod of Example 17 or Example 18, wherein the wireless connectivity protocol comprises a Bluetooth protocol.

Example 20

The convertible entertainment pod of any preceding Example further comprising a control panel for adjusting one or more components of the convertible entertainment pod.

Example 21

The convertible entertainment pod of Example 20, wherein the control panel comprises a graphical user interface.

Example 22

The convertible entertainment pod of any preceding Example, wherein the inner surface of the shell comprises a texture.

Example 23

The convertible entertainment pod of Example 22, wherein the texture reduces echo and/or reverberation of an audio signal provided within the convertible entertainment pod.

Example 24

The convertible entertainment pod of any preceding Example, wherein the inner surface of the shell comprises at least one shelf.

Example 25

The convertible entertainment pod of any preceding Example, wherein the seat portion is adjustable and/or replaceable.

Example 26

The convertible entertainment pod of any preceding Example further comprising at least one seating cushion.

Example 27

The convertible entertainment pod of any preceding Example further comprising a control for selectably enabling and preventing rotational freedom of the shell relative to the stand

Example 28

The convertible entertainment pod of Example 27, wherein the control for selectably enabling and preventing rotational freedom is accessible to a user within the convertible entertainment pod while the convertible entertainment pod is in a first, enclosed configuration.

Example 29

The convertible entertainment pod of Example 27, wherein the control for selectably enabling and preventing rotational freedom prevents a user within the convertible entertainment pod from enabling rotational freedom while the convertible entertainment pod is in a first, enclosed configuration.

Example 30

The convertible entertainment pod of any preceding Example further comprising a solar panel for providing electrical power to at least one electrical feature or component associated with the pod.

Example 31

A method of providing a virtual reality environment to a user, the method comprising providing a convertible entertainment pod to the user, wherein the convertible entertainment pod comprises:
  a shell comprising an inner surface, an outer surface, and a closeable door;
  a base rotatably affixed to the outside surface of the shell;
  one or more sensors for detecting a position and/or movement of at least a portion of the user; and
  an optional a seating portion affixed to or integrated into the inner surface of the shell,
  wherein the convertible entertainment pod adopts a first, enclosed configuration when the closeable door is in a closed position.

Example 32

The method of Example 31, wherein the inner surface is configured to accommodate a virtual reality system.

Example 33

The method of Example 31 or Example 32, wherein the convertible entertainment pod has dimensions suitable to enable a user to freely stand or sit to interact with the virtual reality system.

Example 34

The method of any one of Examples 31-33, wherein the convertible entertainment pod further comprises a video display.

Example 35

The method of Example 34, wherein the video display is mounted to or incorporated into an inner surface of the closeable door.

Example 36

The method of any one of Examples 31-35, wherein the convertible entertainment pod further comprises active noise cancellation for reducing a decibel level outside the convertible entertainment pod.

Example 37

A method of treating a subject in need thereof, the method comprising administering a therapeutic environment to the subject via a convertible entertainment pod, wherein the convertible entertainment pod comprises:
- a shell comprising an inner surface, an outer surface, and a closeable door;
- a base rotatably affixed to the outside surface of the shell;
- one or more sensors for detecting a position and/or movement of at least a portion of the user; and
- an optional a seating portion affixed to or integrated into the inner surface of the shell,
- wherein the convertible entertainment pod adopts a first, enclosed configuration when the closeable door is in a closed position.

Example 38

The method of Example 37, wherein the therapeutic environment comprises aromatherapy, light therapy, oxygen therapy, and/or reduced ambient noise.

Example 39

The method of Example 37 or Example 38, wherein the convertible entertainment pod further comprises a ventilation system for providing an aromatherapy or oxygen therapy atmosphere to the subject.

Example 40

The method of any one of Examples 37-39, wherein the convertible entertainment pod further comprises at least one light secured to the inner surface of the shell for providing light therapy to the subject.

Example 41

The method of any one of Examples 37-40, wherein the convertible entertainment pod provides noise cancellation for providing reduced ambient noise to the subject.

Example 42

The method of Example 41, wherein the noise cancellation provides sound masking.

Example 43

The method of Example 42, wherein the sound masking comprises introducing white noise to an interior of the convertible entertainment pod.

Example 44

The method of Example 42, wherein the sound masking comprises introducing pink noise to an interior of the convertible entertainment pod.

Example 45

A method of providing sleep therapy to a subject in need thereof, the method comprising providing a convertible entertainment pod to the subject, wherein the convertible entertainment pod comprises:
- a shell comprising an inner surface, an outer surface, and a closeable door;
- a base rotatably affixed to the outside surface of the shell;
- one or more sensors for detecting a position and/or movement of at least a portion of the user; and
- a seating portion affixed to or integrated into the inner surface of the shell,
- wherein the convertible entertainment pod adopts a first, enclosed configuration when the closeable door is in a closed position.

Example 46

The method of Example 45, wherein the convertible entertainment pod provides noise cancellation for providing reduced ambient noise to the subject.

Example 47

The method of Example 46, wherein the noise cancellation comprises active noise cancellation for reducing a decibel level outside the convertible entertainment pod.

Example 48

The method of Example 46 or Example 47, wherein the noise cancellation provides sound masking.

Example 49

The method of Example 48, wherein the sound masking comprises introducing white noise to an interior of the convertible entertainment pod.

Example 50

The method of Example 48, wherein the sound masking comprises introducing pink noise to an interior of the convertible entertainment pod.

The invention claimed is:

1. A method for privately accessing video or audio content, the method comprising:
   entering a convertible pod, wherein the convertible pod includes a two-piece shell;
   adjusting said convertible pod to adopt an enclosed configuration, wherein said convertible pod comprises an acoustical insulating layer for increasing a decibel differential between an interior portion of said convertible pod and an exterior portion of said convertible pod such that a decibel level in the exterior portion of said convertible pod is lower than a decibel level in the interior portion of said convertible pod;
   accessing video or audio content while said convertible pod is in said enclosed configuration;
   adjusting interior lighting of said convertible pod by adjusting a lighting setting of said convertible pod; and
   wherein said convertible pod comprises at least one video projector and at least one speaker; and
   wherein said convertible pod further comprises a seating portion affixed to or integrated into an inner surface of said convertible pod.

2. The method of claim 1, wherein accessing said video or audio content is accomplished by syncing, either through a wired or wireless connection, a mobile device with said convertible pod, and accessing said video or audio content through said mobile device.

3. The method of claim 1, wherein accessing said video or audio content is accomplished through a user interface integrated into said convertible pod.

4. The method of claim 1, wherein said convertible pod includes a base rotatably coupled to an outside surface of said convertible pod.

5. The method of claim 1, wherein said convertible pod includes a closeable door, and wherein said convertible pod is configured to completely enclose a user when the closeable door is in a closed position.

6. The method of claim 1, wherein said convertible pod further comprises at least one microphone.

7. The method of claim 1, further comprising adjusting the temperature of said convertible pod by adjusting a heating or cooling setting of said convertible pod.

8. The method of claim 1, wherein an outer surface of said convertible pod further comprises a solar panel configured to provide power to said convertible pod.

9. The method of claim 1, wherein said convertible pod further comprises at least one sensor for detecting a position or movement of at least a portion of a user interacting with a virtual or augmented reality system.

10. The method of claim 1, wherein the convertible pod further comprises wheels, wherein the wheels automatically lock when a weight above a threshold weight is added to the convertible pod.

11. The method of claim 1, wherein, the decibel level in the exterior portion of said convertible pod in the enclosed configuration is a first decibel level, and wherein the first decibel level is different from a second decibel level in another configuration of the convertible pod.

12. A method of treating a subject, the method comprising administering a therapeutic environment to the subject via a convertible pod, wherein the convertible pod comprises:
   a two-piece shell comprising an inner surface, an outer surface, and a closeable door; and
   a seating portion affixed to or integrated into the inner surface of the shell, wherein the seating portion is capable of being positioned in a reclined configuration;
   wherein the convertible pod can be converted into an enclosed configuration by the closeable door being placed into a closed position;
   wherein the convertible pod comprises at least one light secured to the inner surface of the shell; and
   wherein the convertible pod comprises an acoustical insulating layer for increasing a decibel differential between an interior portion of the convertible pod and an exterior portion of the convertible pod such that a decibel level in the exterior portion of the convertible pod is lower than a decibel level in the interior portion of the convertible pod.

13. The method of claim 12, wherein the convertible pod further comprises a ventilation system for providing an aromatherapy therapy to the subject.

14. The method of claim 12, wherein the convertible pod is configured to hold only one subject at a time.

15. The method of claim 12, wherein the convertible pod provides noise cancellation, wherein the noise cancellation comprises sound masking.

16. The method of claim 12, wherein the convertible pod provides noise cancellation, wherein the noise cancellation comprises active noise cancellation.

17. The method of claim 12, wherein the convertible pod further comprises a heating/cooling system that incorporates a heating coil and/or air conditioning system.

18. The method of claim 12, wherein the outer surface of the convertible pod further comprises a solar panel configured to provide power to the convertible pod.

19. The method of claim 12, wherein the convertible pod further comprises wheels, wherein the wheels automatically lock when a weight above a threshold weight is added to the convertible pod.

20. A method for privately accessing video or audio content, the method comprising:
   entering a convertible pod;
   adjusting said convertible pod to adopt an enclosed configuration;
   accessing video or audio content while said convertible pod is in said enclosed configuration, wherein accessing said video or audio content is accomplished by syncing, either through a wired or wireless connection, a mobile device with said convertible pod, and accessing said video or audio content through said mobile device;
   adjusting interior lighting of said convertible pod by adjusting a lighting setting of said convertible pod; and
   adjusting the temperature of said convertible pod by adjusting a heating or cooling setting of said convertible pod;
   wherein said convertible pod comprises at least one video projector and at least one speaker;
   wherein said convertible pod further comprises a seating portion affixed to or integrated into an inner surface of said convertible pod, wherein said seating portion is capable of being positioned in a reclined configuration; and
   wherein said convertible pod further comprises an acoustical insulating layer for increasing a decibel differential between an interior portion of said convertible pod and an exterior portion of said convertible pod such that a decibel level in the exterior portion of said convertible pod is lower than a decibel level in the interior portion of said convertible pod.

* * * * *